(12) United States Patent
Turbe et al.

(10) Patent No.: US 11,079,329 B2
(45) Date of Patent: Aug. 3, 2021

(54) HUMAN WASTE WATER AND HUMAN-DERIVED PATHOGEN SCOUTING TOOL

(71) Applicant: University of North Carolina Wilmington, Wilmington, NC (US)

(72) Inventors: Mary M. Turbe, Wilmington, NC (US); Lawrence B. Cahoon, Wilmington, NC (US)

(73) Assignee: University of North Carolina Wilmington, Wilmington, NC (US)

( * ) Notice: Subject to any disclaimer, the term of this patent is extended or adjusted under 35 U.S.C. 154(b) by 180 days.

(21) Appl. No.: 16/143,640

(22) Filed: Sep. 27, 2018

(65) Prior Publication Data

US 2019/0094144 A1    Mar. 28, 2019

Related U.S. Application Data

(60) Provisional application No. 62/563,680, filed on Sep. 27, 2017.

(51) Int. Cl.

| | |
|---|---|
| *G01N 21/64* | (2006.01) |
| *G01N 33/18* | (2006.01) |
| *G01N 1/34* | (2006.01) |
| *G01N 1/40* | (2006.01) |

(52) U.S. Cl.
CPC .............. *G01N 21/643* (2013.01); *G01N 1/34* (2013.01); *G01N 1/4055* (2013.01); *G01N 21/64* (2013.01); *G01N 33/18* (2013.01); *G01N 2001/4061* (2013.01); *G01N 2021/6439* (2013.01); *Y10T 436/255* (2015.01)

(58) Field of Classification Search
CPC ............ G01N 1/34; G01N 1/40; G01N 1/405; G01N 1/4055; G01N 2001/4061; G01N 2021/6439; G01N 21/64; G01N 21/643; G01N 33/18; Y10T 436/25; Y10T 436/25125; Y10T 436/25375; Y10T 436/255

USPC .......... 436/39, 164, 166, 172, 174, 175, 177, 436/178; 422/82.05, 82.08, 527, 534
See application file for complete search history.

(56) References Cited

U.S. PATENT DOCUMENTS

| 5,298,392 A | * | 3/1994 | Atlas ..................... C12Q 1/689 435/6.14 |
| 2011/0186753 A1 | | 8/2011 | Dixon |

FOREIGN PATENT DOCUMENTS

| GB | 2576949 | * | 3/2020 |
| WO | 2006033321 A1 | | 3/2006 |

OTHER PUBLICATIONS

Vinodgopal, K. et al. Abstract from Abstracts, 38th Great Lakes Regional Meeting of the American Chemical Society, Chicago, IL, United States, May 13-16, 2009.*
Shu et al. Journal of Chromatography A, vol. 1088, Feb. 3, 2005, pp. 218-223.*
Poiger et al. Environ. Sci. Technol., vol. 30, 1996, pp. 2220-2226.*
International Search Report and Written Opinion issued in counterpart PCT Application No. PCT/US2018/053014 dated Jan. 24, 2019 (eleven (11) pages).
Hartel et al. "Exposing water samples to ultraviolet light improves fluorometry for detecting human fecal contamination" Water Research. 2007; p. 281 col. 1 para [0001]; p. 282 col. 1 para[0001]; p. 283 col. 1 para (0001]; p. 285 col. 2 para[0004]; p. 286 col. 1 para[0001]-[0002]; p. 292 col. 2 para[0002]; p. 294 col. 2 para[0002].
Hartel et al. "Combining targeted sampling and fluorometry to identify human fecal contamination in a freshwater creek" Journal of Water and Health. vol. 6(1 ). 2008. pp. 1 05-116; Especially Abstract.
Allfrey et al. "A Fluorometric Method for the Determination of Pteroylglutamic Acid" Journal of Biological Chemistry. 1949. vol. 178. pp. 465-481; Especially p. 473 para[0005].

\* cited by examiner

*Primary Examiner* — Maureen Wallenhorst
(74) *Attorney, Agent, or Firm* — E. Eric Mills; Nexsen Pruet, PLLC

(57) ABSTRACT

The present subject matter provides processes and kits for identifying the presence of waste water or human-derived pathogens, particularly those associated with the presence of human fecal matter, in surface or subsurface water sources.

13 Claims, No Drawings

HUMAN WASTE WATER AND HUMAN-DERIVED PATHOGEN SCOUTING TOOL

CROSS-REFERENCE TO RELATED APPLICATIONS

The presently disclosed subject matter is related to and claims priority to U.S. Provisional Patent Application No. 62/563,680 entitled "Human Waste Water and Human-Derived Pathogen Scouting Tool" filed on Sep. 27, 2017; the entire disclosure of which is incorporated herein by reference.

BACKGROUND

The United States Environmental Protection Agency and many related state and municipal agencies provide clean water criteria for human use and consumption. Human waste in the form of fecal matter and the attendant well-defined pathogens (see, e.g., *Contaminant Candidate List 3, Microbes: PCCL to CCL Process*, United States Environmental Protection Agency, February 2008) are among the many concerns for pollutants and impurities frequently found in surface and subsurface water. Such contaminants may be present before or, on occasion, following water treatment intended to remove these contaminants. A significant challenge, following the identification of the presence of such contaminants, is identification of the point source and mitigation efforts to control further pollution.

A broad range of tests for fecal matter and associated pathogens have been developed by the scientific community. For example, Scott, et al. (Scott, T. Rose, J., Jenkins, T., Farrrah, S and Lukasik, J. (2002). Microbial Source Tracking: Current Methodology and Future Directions, *Applied and Environmental Microbiology*, 68(12): 5796-5803) references multiple methods for determining the presence and origin of fecal matter including, for example, microbiological, genotypic, phenotypic and chemical tracers. Although each method has its attributes, none of these methods provide a rapid field test that provides on-site results. Accordingly, the present invention provides for processes that can be deployed at the site of sampling and kits containing some or all of the material required to carry out such processes.

SUMMARY

The present invention provides processes for identifying the presence of human-derived pathogens, particularly those associated with the presence of human fecal matter, in surface or subsurface water sources. Such water sources can be natural or human-made. The present invention further provides kits assembled for the afore-mentioned determination. The processes and kits of the present invention can be used for analyzing water samples where human-derived pathogens and, typically, optical brighteners contained in laundry detergents coexist in, without limitation, ponds, rivers and streams, lakes, standing water, outflow from septic systems and other naturally occurring or human-made water sources.

DETAILED DESCRIPTION

Definitions

"Contaminants" means human fecal matter and/or associated human pathogens. "Human pathogens in water" means those pathogen associated with human waste, without limitation, as elucidated and enumerated in *Contaminant Candidate List 3, Microbes: PCCL to CCL Process*, United States Environmental Protection Agency, February 2008. "Optical Brighteners" means optical brightening agents (OBAs), fluorescent brightening agents (FBAs) and/or fluorescent whitening agents (FWAs). Optical Brighteners are dyes that absorb light in the ultraviolet and violet region (usually 340-370 nm) of the electromagnetic spectrum, and re-emit light in the blue region (typically 420-470 nm) and are typically used in laundry detergents to enhance the appearance of color of fabric or paper. Non-limiting examples of optical brighteners include 1,3,6,8-pyrene sulfate and 4,4-diamino-2,2stilbenedisulfonic acid. "Point Source" means the location at which contaminants enter surface or subsurface water. "Solid Phase Extraction" has the traditional meaning in the chemical arts. "Solid Phase Extraction Cartridge" has the traditional meaning in the chemical arts. "Sunlight Resistant Container(s)" means any container or vial that inhibits or prohibits transmittance of sunlight to the content of such container when exposed to indigenous or artificial sunlight.

"Water Sample(s)" means one or more aliquot of water collected from a chemically treated or untreated surface or subsurface water source.

"Waste Water" means water that could be contaminated with human waste and associated pathogens that has not been treated for the removal of such contaminants.

While the present disclosure is susceptible to various modifications and alternative forms, example embodiments are herein described. It should be understood, however, that the description of specific teachings and/or example embodiments is not intended to limit the invention to the particular forms disclosed, but on the contrary, this disclosure is to cover all modifications and equivalents as defined by the appended claims.

One aspect of the present invention provides a process for identifying the presence of human pathogens in waste water samples containing optical brighteners comprising the steps of: collecting a water sample; running the waste water sample through the solid phase extraction cartridge; reducing interference of naturally occurring fluorescing compounds; concentrating and enhancing the fluorescence signal of optical brighteners; and determining the presence of the optical brighteners, optionally comprising a filtering step following the collection step.

Another aspect of the present invention provides a process for identifying the presence of human fecal matter and associated pathogens in water samples containing optical brighteners comprising the steps of: collecting a water sample; running the water sample through the solid phase extraction cartridge; reducing interference of naturally occurring fluorescing compounds; concentrating and enhancing the fluorescence signal of optical brighteners; and determining the presence of the optical brighteners, optionally comprising a filtering step following the collection step.

A further aspect of the present invention provides a kit for detecting waste water or human fecal matter and associated pathogens in water samples comprising: at least one solid-phase extraction cartridge; at least one aliquot of at least one weak base; and at least one aliquot of at least one polar organic solvent, optionally including: a filtration system, at least one fitting for a solid-phase extraction cartridge, at least one sunlight resistant container, optical brightener absorbing packing material for the solid-phase extraction cartridge, directions for use and a fluorometric detector. Alternatively, the solid phase extraction cartridge can be prepacked with the optical brightener absorbing packing material. Accordingly, the present kits can include a plurality of one or more of these kit components.

The processes of the present invention are carried out step-wise. Initially, at least one water sample is collected. If the sample is to be immediately tested, proceed to the following steps. If the sample is to be stored for later testing, the sample should be stored in a sunlight resistant container to limit further deterioration or break down of the optical brighteners in such samples. When the determining the presence of the optical brighteners step is to be carried out in a location other than in the field, samples collected from the concentrating and enhancing the fluorescence signal of optical brighteners step may also be stored in a sunlight resistant container.

Standards for optical brighteners may be prepared. Typically, the optical brightener is dissolved in a weak base before the subsequent steps of the instant process are conducted. Optical brightener concentrations are in the range of about 10 to about 1000 ppb, dissolved in about 25 mL to about 50 mL of weak base in the molar range of about 0.01 M to about 0.02M. The weak base is any weak base that would dissolve the optical brighteners and include, without limitation, ammonia, ammonium hydroxide and the like.

Following the collection step, water samples are optionally and typically filtered to remove large particles and unwanted material providing such filtration does not minimize or remove the targeted contaminants. Such filters and filtration systems, with or without a suction component, are well known in the art.

Solid phase extraction cartridges can be prepared via well-known means or purchased with appropriate packing. Appropriate packing for the present processes includes any material that will selectively partition optical brighteners from other dissolved organic material. Such packing can be selected from cotton and a variety of cellulosic packing materials, typically a powder form of a long-fiber cellulose such as, for example and without limitation, CF 11 cellulose. CF 11 Cellulose is available from a multitude of suppliers (e.g., Sigma-Aldrich, St. Louis, Mo.; Whatman (GE Life Sciences) Pittsburgh, Pa.; and Cole Parmer, Vernon Hills, Ill.). The solid phase extraction cartridges can be fitted with pumps or syringes for positive-pressure flow or reservoirs that can be used with vacuum-assisted flow.

The water sample is then pulled or pushed through the solid phase extraction cartridge, effectively retaining optical brighteners and associated contaminants, among other organic-based material. Humic acids found in nature are frequently contained in such water samples. The fluid remaining after this step may be discarded, retained for future use or run through the solid phase extraction cartridge one or more additional times. The reducing interference of naturally occurring fluorescing compounds step comprises at least one elution of non-optical brightener-associated organic-based materials retained in the solid phase extraction cartridge, particularly humic acids and other natural fluorescing compounds, using a dilute base such as NaOH and equivalents thereof. Other bases that can be used for this step include, without limitation, potassium hydroxide, ammonium hydroxide, sodium carbonate and the like. As used herein, the term dilute base means from about 0.01N to about 0.05N. The eluent from this step can also be discarded.

The concentrating and enhancing the fluorescence signal of optical brighteners step is accomplished via elution of the optical brighteners using a polar organic solvent. Such polar organic solvents include, without limitation, methanol, ethanol, propanol, and the like.

Such polar organic solvents are used as eluents for the present step in a ratio of from about 1:1 to about 30:1, from about 1:1 to about 20:1; about 1:1 to about 15:1; from about 1:1 to about 10:1; and about 1:1 to about 5:1 original water sample volume to eluent volume. Typically a ratio of about 10:1 original water sample to eluent volume is used. Alternatively, a non-polar organic solvent, such as, for example and without limitation polyethylene glycol 400 (PEG 400) can be used to carry out the concentrating and enhancing the fluorescent signal of optical brighteners step either alone or in combination with a polar organic solvent. Such non-polar organic solvents are used as eluents for the present step in concentrations of from about 100% to about 20% with concentrations of less than 100% being diluted with water, typically deionized water. Other concentrations of such polar organic solvents for the present step include from about 80% to about 20%, from about 75% to about 30%, from about 60% to about 40%, and concentrations of about 100%, about 50% and about 30%. It was discovered that the use of these solvents are useful eluents for the extraction of the optical brighteners associated with contaminants from the solid phase extraction cartridge, but also concentrates and enhances the fluorescent signal of the optical brighteners. For the polar organic solvents, ethanol is particularly useful for such concentration and enhancing while ethanol is safer than methanol to use. As such, selection of the polar organic solvent and/or non-polar organic solvents is left to the discretion of the individual implementing the present processes.

It has been determined that contaminants, as defined above and used herein, are typically associated with optical brighteners when both are present in water samples. By determining the presence of optical brighteners, by inference, waste water and associated pathogens or human fecal matter and associated pathogens are selectively identified as being present in the water sample. Without being held to any particular theory, because optical brighteners absorb near-UV light and glow in the visible range of light, particularly the blue portion, this absorption-emission behavior is responsible for the sensitive fluorescence detection of these compounds and for their utility as a sensitive tracer for the presence of waste water and associated pathogens and human fecal matter, and associated pathogens in surface and subsurface water.

Accordingly, the eluent from the immediately preceding step is used in determining the presence of the optical brighteners step of the present processes. An aliquot of the eluent is subjected to a fluorometric detector. Such detectors, and processes for the use thereof, are well known and well used in the art, and a broad range of fluorometric detectors are commercially available. Fluorescence is a positive indicator of the presence of human waste and, potentially, and likely, associated pathogens.

An additional aspect of the present invention provides for kits for detecting human fecal matter and associated pathogens in water samples comprising: at least one solid-phase extraction cartridge; optical brightener absorbing packing material for the solid-phase extraction cartridge; at least one aliquot of at least one weak base; at least one aliquot of at least one polar and/or non-polar organic solvent; and directions for the use of such kits; optionally including a filtration system; at least one sunlight resistant container; at least one fitting for a solid-phase extraction cartridge; and a fluorometric detector, typically a portable fluorometric detector. Alternatively and typically, the solid phase extraction cartridge can be pre-packed with the optical brightener absorbing packing material.

Kits can include one of each of the materials described above or multiples of one or more such materials for enhanced and multiple test samples to be examined. Accordingly, the kits of this invention can include a plurality of each of the packed or unpacked solid-phase extraction cartridge, optical brightener absorbing packing material for unpacked solid phase extraction cartridges, the weak base, and a solvent selected from the group consisting of a polar organic solvent and a non-polar organic solvent and, optionally, one or more of the filtration system, the sunlight resistant containers, the fitting for a solid-phase extraction cartridge, and the fluorometric detector.

Each of the materials provided in the kits are as described above or are well known in the art. Quantities of materials provided in the kits are sufficient for the number of samples for which the kit is designed, typically with excess provided for the weak base and polar organic solvent and/or non-polar organic solvent. Alternatively, multiple pre-measured aliquots of the weak base and polar organic solvent and/or non-polar organic solvent, sufficient to complete one process of the present invention, multiple times, are provided. Certain of the kit materials can be used multiple times such as, for example, the filtration system, sunlight resistant containers and fittings for the solid-phase extraction cartridge provided due care is used to avoid contamination from one water sample to subsequent water samples.

In addition, the processes and kits of the present invention can be utilized for testing water samples from various locations of the same water source to aid in determining the point source of human waste and associated pathogens. These processes and kits can be used in field setting providing real-time, rapid results. Accordingly, use of the present process provides a safe, cost-effective and selective method for determining the presence of waste water and associated pathogens and human fecal matter and associated pathogens.

The following examples are intended only for the purpose of exemplification and are not intended to limit the scope or teachings of the instant application in any manner whatsoever.

EXAMPLES

Example 1: The following represents the iterative process used to identify and verify certain aspects of the present invention:

Methods/Processes and Materials

A fluorometer excites in the UV light range and then measures emissions in the visible blue light spectrum. This study used the Turner Trilogy fluorometer with an optical brightener module (model #7200-047) that was calibrated in parts per billion using 1,3,6,8-pyrene tetra sulfate, an optical brightener compound. Absorbance measurements were taken with a spectrophotometer at a wavelength of 490 nm. For statistical tests, alpha was <0.05.

Optical Brightener Concentration

A variety of liquid laundry detergents were mixed with deionized water (DI water) to make 1/10,000 dilutions. The fluorescence of four samples for each detergent were tested. The following detergents were tested: Cheer® Stay Colorful, Purex® No Sort for Colors, Tide® Simply Clean and Fresh, Tide® Coldwater Clean, Total Home® 2× Concentrated, Gain®, Downy®, LA's Totally Awesome® Laundry Detergent. The data were analyzed with a one-way ANOVA to determine if there was significant variance between the fluorescence measurements of different laundry detergents. If there was significant variance, then a Tukey comparison of means was used to see which detergents were significantly different from each other.

Degradation of Optical Brighteners

The degradation over time of 1/10,000 dilutions of four laundry detergent brands (Cheer®, Tide®, Gain® and Total Home®) was tested. A solution was also made with 0.01 g of an optical brightener chemical, 4,4-Diamino-2,2'-stilbenedisulfonic acid, that was dissolved into 100 mL of 0.01 M NaOH, and then diluted with one liter of DI water (referenced as OB Compound). The final concentration of 4,4-Diamino-2,2'-stilbenedisulfonic acid was 0.00002 M. The original fluorescence of each solution was measured three times. They were then exposed to indoor sunlight and the fluorescence was measured in triplicate at 15 minutes, 30 minutes, 45 minutes, and 24 hours. These data were averaged per laundry detergent at each time period, and then percent of the original fluorescence remaining was calculated and plotted.

The degradation rates of two laundry detergent "packs", Total Home Laundry Detergent Packs and Tide Pods, were also tested. The packs were dissolved in 300 mL of DI water, and then a 1/10,000 dilution was made with the dissolved pack solutions and DI water. Their original fluorescence was measured three times, then the solutions were exposed to indoor sunlight. Additional triplicate measurements were taken after 15 minutes, 30 minutes, 45 minutes, 24 hours, 72 hours, 96 hours, 144 hours, 264 hours, 504 hours, 576 hours, 624 hours, 672 hours, and 744 hours. Exponential curves were fit to these data.

Developed Methods/Processes

Once water samples were collected, they were filtered to remove debris and stored in light proof containers in a cooler until tested. The samples were returned to ambient temperature before being tested. The original fluorescence and absorbance were measured from triplicate samples before 50 mL of the sample were pulled through a solid phase extraction cartridge packed with 1 g of CF11 Cellulose. Fluorescence values that were greater than DI water blanks indicated the presence of optical brighteners and/or humic acids.

Absorbance values that were greater than the values of DI water blanks were used to track the presence of humic acids because they have color. Triplicate measurements were taken of the absorbance and fluorescence of what came out of the column for comparison. 5 mL of DI water was pulled through the column and then its absorbance and fluorescence was measured. Finally, 10 mL of methanol was run through the column to rinse the optical brighteners out. The absorbance and fluorescence were then measured in triplicates. In order to compare the amount of optical brighteners that were coming through in each step and eliminate any concentration effect, percent of the original fluorescence was calculated using $100*[(v_n*F_n)/(50*F_o)]$, where v=volume (mL), F=fluorescence (ppb), and n represents the step. The 50 represents the original 50 mL of solution that was pulled through the column. There were three steps: after column, DI rinse, and methanol rinse. The percent of the original absorbance for each step was calculated using the same formula as fluorescence.

Water samples from nature were collected from areas that were suspected not to be impacted by human waste and were high in humic acids, and were used as a control. These samples were collected from in and around Wilmington, N.C., including Colly Creek and the University of North Carolina Wilmington campus. Additional samples were collected from areas that were believed to be impacted by human waste. These areas include Molts Creek, Pump Station 34, Bay Shore, Randall Pond, and the stream off Rosemont Avenue that drains into Randall Pond.

Natural water was spiked with laundry detergent dilutions in order to validate these processes. 25 mL of natural water (prepared in the same manner as explained above), and 25 mL of a 1/10,000 laundry detergent dilution were mixed together. Fluorescence and absorbance of each component were measure before being mixed. Once they were mixed, fluorescence and absorbance were measured, which was used as the original solution levels for calculation. The samples are referred to as mixed samples. One-way ANOVA was used to compare the percent of the original fluorescence after each step of the processes, for all mixed samples, natural water samples, and field samples separately, and all samples combined. A Tukey test was used to compare means of the process steps if the one-way ANOVA was significant. A two way analysis of variance was used to compare the effects of sample types and process step on fluorescence, including the interaction effect of sample type x process step. The exact same ANOVA tests were then used to analyze the absorbance values.

Methanol Boosting

The effect of methanol on the fluorescence of optical brighteners and natural fluorescing organic matter was tested using a methanol dilution series. Methanol was mixed with quantified laundry detergent dilutions, the OB Compound, and natural water at specified ratios, and triplicate fluorescence measurements were taken ten minutes after the solutions were mixed. DI water was used as a control and tested with the same procedure. Multiple linear regression analyses with two x variables were used to determine if the solvent and the relative concentrations significantly impacted fluorescence values.

Results

Optical Brightener Concentration

There was a significant difference in optical brightener concentrations among different liquid laundry detergent brands (F=70.7, p<0.0001). There was a 909 ppb range from the laundry detergent with highest fluorescence (Tide Coldwater Clean) to the laundry detergent with the lowest fluorescence (LA's Totally Awesome). The results of the Tukey test indicate which laundry detergents were significantly different from each other. Although there were extremes on both ends, most of the detergents were similar in optical brightener content.

Degradation of Optical Brighteners

The fluorescence values after 15 minutes were, on average, 69.6 percent lower than original fluorescence. Specifically for laundry detergents, the average degradation after 15 minutes was 64.6 percent. After 24 hours, they went down 72.8 percent on average with a range of 30.8-92.0 percent.

The laundry detergent "packs" degraded in an exponential matter. The Tide Pods had an $R^2$ of 0.988, and the Total Home had and $R^2$ of 0.776, indicating that these exponential curves account for most of the variation in fluorescence.

Developed Methods/Processes

The one-way ANOVA for each sample type's fluorescence and absorbance values showed significant differences between the process steps. Each step of the solid phase extraction process yielded significantly different fluorescence responses for mixed samples and all the data combined. Natural and field samples did not have statistically different fluorescence values between the two rinse steps, but the after column step was significantly different. All data sets had absorbance values for the after column step that were significantly different from both rinse steps, but the rinse steps were not different from each other.

The two-way ANOVA test for fluorescence indicated the sample type and the process step both had significant impacts on the fluorescence values. It also showed that there was an interaction effect between the type of samples and the steps of the process. The two-way ANOVA for absorbance, however, showed no interaction effect between the samples and steps. Separately, both the sample type and the process step had significant effects on the absorbance values. The greatest absorbance came out after the after column step for each type of sample, followed by a similar percent coming through in each of the rinse steps.

Methanol Boosting

The p-values, with the exception of the 1/1,000 dilution of Cheers® relative concentration, were less than 0.05, concluding there is a statistical significant relationship between the solvent for all tests and the relative concentration for all samples except the 1/1,000 dilution of Cheer°. When the solutes were mixed with methanol, they had higher fluorescence values than when they were mixed with water. This indicates there is a solvent effect between methanol and optical brighteners.

Additional Methods/Processes and Materials

Non-Polar Organic Solvent

This study also used the Turner Trilogy fluorometer with an optical brightener module (model #7200-047), but measurements were taken in raw fluorescent units (RFUs).

In addition to polar solvents, the non-polar organic solvent polyethylene glycol 400 (PEG 400) was tested in the developed methods/processes to test effectiveness of rinsing optical brighteners out of the column and boosting their signal. PEG 400 was measured at 4 strengths: 100% PEG 400, 50% PEG 400 and 50% DI Water, 30% PEG 400 and 70% DI Water, and 10% PEG 400 and 90% DI Water.

10 mL of the solvent was used with the appropriate amount of deionized water to prepare the concentrations set forth above. The PEG 400 is effective at rinsing optical brighteners out of the column and enhancing the fluorescent signal when the total fluorescence value is about 500% of the original samples. As such, PEG 400 is effective at both rinsing the optical brighteners and enhancing their fluorescence, its fluorescence will be greater than 500% of the originals samples.

Results

Non-Polar Organic Solvent

The 10% PEG 400 dilution's fluorescence was 268%, and therefore did not effectively rinse the optical brighteners out of the column and enhance the fluorescent signal. The Methanol, 30%, 50% and 100% PEG 400 dilutions all fluoresced over 1500% of the original samples fluorescence, demonstrating that non-polar organic solvents at varying concentration ranges are effective at rinsing and enhancing the signal of optical brighteners present in water samples (in order, 4265%, 1500%, 1536%, and 1610%).

That which is claimed:

1. A process for identifying a presence of human fecal matter in water samples, the process comprising:
 collecting a water sample, the water sample containing optical brighteners;
 running the water sample through a solid phase extraction cartridge;
 reducing interference of naturally occurring fluorescing compounds by at least a first elution of the naturally occurring fluorescing compounds from the extraction cartridge while retaining at least a portion of the optical brighteners;

concentrating and enhancing a fluorescence signal corresponding to the optical brighteners, by at least a second elution of the optical brighteners from the extraction cartridge; and determining a presence of the optical brighteners based on a detection of the fluorescence signal, wherein the presence of the optical brighteners indicates the presence of human fecal matter in the water sample.

2. The process of claim 1, wherein a presence of pathogens associated with human fecal matter is also identified based on the fluorescence signal.

3. The process of claim 2, further comprising filtering the water sample prior to running the water sample through the extraction cartridge.

4. The process of claim 3, wherein the at least first elution is carried out using a dilute base.

5. The process of claim 4, wherein the dilute base is sodium hydroxide.

6. The process of claim 3, wherein the concentrating step is carried out using at least one of a polar organic solvent and a non-polar organic solvent.

7. The process of claim 6, wherein the polar organic solvent is selected from the group consisting of methanol and ethanol.

8. The process of claim 6, wherein the non-polar organic solvent is polyethylene glycol (PEG) 400.

9. The process of claim 3, wherein the determining step is carried out using a fluorometric detector.

10. The process of claim 3, wherein the reducing step is carried out using a dilute base, the concentrating step is carried out using a solvent selected from the group consisting of a polar organic solvent and a non-polar organic solvent, and wherein the determining step is carried out using a fluorometric detector.

11. The process of claim 10, wherein the dilute base is sodium hydroxide, the polar organic solvent is selected from the group consisting of methanol and ethanol and the non-polar organic solvent is polyethylene glycol (PEG) 400.

12. A process for identifying a presence of waste water in water samples, the process comprising:
  collecting a water sample the water sample containing optical brighteners;
  running the water sample through a solid phase extraction cartridge;
  reducing interference of naturally occurring fluorescing compounds by at least a first elution of the naturally occurring fluorescing compounds from the extraction cartridge while retaining at least a portion of the optical brighteners;
  concentrating and enhancing a fluorescence signal associated with the optical brighteners, by at least a second elution of the optical brighteners from the extraction cartridge; and
  determining a presence of the optical brighteners based on a detection of the fluorescence signal, wherein the presence of the optical brighteners indicates the presence of waste water.

13. The process of claim 12, wherein a presence of human pathogens associated with waste water is also identified based on the fluorescence signal.

* * * * *